United States Patent
Demmer et al.

(10) Patent No.: US 9,308,376 B2
(45) Date of Patent: Apr. 12, 2016

(54) METHOD AND APPARATUS FOR DETECTING LOSS OF CAPTURE

(71) Applicant: Medtronic, Inc., Minneapolis, MN (US)

(72) Inventors: Wade M Demmer, Coon Rapids, MN (US); Douglas A Peterson, Apple Valley, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 14/248,646

(22) Filed: Apr. 9, 2014

(65) Prior Publication Data

US 2015/0238769 A1    Aug. 27, 2015

Related U.S. Application Data

(60) Provisional application No. 61/912,189, filed on Feb. 24, 2014.

(51) Int. Cl.
| | | |
|---|---|---|
| A61B 5/04 | (2006.01) | |
| A61N 1/37 | (2006.01) | |
| A61N 1/39 | (2006.01) | |
| A61N 1/362 | (2006.01) | |
| A61N 1/372 | (2006.01) | |

(52) U.S. Cl.
CPC .............. *A61N 1/3712* (2013.01); *A61N 1/371* (2013.01); *A61N 1/362* (2013.01); *A61N 1/37205* (2013.01); *A61N 1/3943* (2013.01); *A61N 1/3956* (2013.01)

(58) Field of Classification Search
CPC ... A61B 5/0006; A61B 5/0452; A61B 5/0468
See application file for complete search history.

(56) References Cited

U.S. PATENT DOCUMENTS

| | | |
|---|---|---|
| 761,162 A | 5/1904 | Gold |
| 4,476,868 A | 10/1984 | Thompson |
| 5,052,388 A | 10/1991 | Sivula et al. |
| 5,165,404 A | 11/1992 | Andersson et al. |
| 5,165,405 A | 11/1992 | Eckwall |
| 5,172,690 A | 12/1992 | Nappholz et al. |
| 5,222,493 A | 6/1993 | Sholder |
| 5,285,780 A | 2/1994 | Tsuji et al. |
| 5,320,643 A | 6/1994 | Roline et al. |
| 5,324,310 A | 6/1994 | Greeninger et al. |

(Continued)

FOREIGN PATENT DOCUMENTS

| | | |
|---|---|---|
| EP | 1 116 495 A2 | 7/2001 |
| EP | 2239007 A1 | 10/2010 |

OTHER PUBLICATIONS (PCT/US2014/067337) PCT Notification of Transmittal of the International Search Report and the Written Opinion of the International Searching Authority.

(Continued)

*Primary Examiner* — Natasha Patel
(74) *Attorney, Agent, or Firm* — Evans M. Mburu

(57) ABSTRACT

A method and apparatus for identifying loss of capture in a pacing device. While pacing pulses are being delivered, the device checks for emergence of a stable asynchronous underlying intrinsic rhythm in the presence of the delivered pacing pulses. The device determines that loss of capture has occurred responsive to emergence of the underlying rhythm. In response to determining that loss of capture has occurred, pacing provided by device is modified, for example by performing a threshold test and adjusting the energy levels of delivered pacing pulses in response thereto.

14 Claims, 15 Drawing Sheets

(56) References Cited

U.S. PATENT DOCUMENTS

| | | | |
|---|---|---|---|
| 5,345,362 A | 9/1994 | Winkler |
| 5,447,525 A | 9/1995 | Powell et al. |
| 5,601,615 A | 2/1997 | Markowitz et al. |
| 5,766,230 A | 6/1998 | Routh et al. |
| 5,782,889 A | 7/1998 | Högnelid et al. |
| 5,944,745 A | 8/1999 | Rueter |
| 5,954,755 A | 9/1999 | Casavant |
| 6,389,316 B1 | 5/2002 | Bornzin et al. |
| 6,553,259 B2 | 4/2003 | Mouchawar et al. |
| 6,772,005 B2 | 8/2004 | Casavant et al. |
| 6,950,704 B1 | 9/2005 | Bradley |
| 7,130,690 B2 | 10/2006 | Rueter et al. |
| 7,280,868 B2 | 10/2007 | Rueter et al. |
| 7,400,924 B2 | 7/2008 | Rueter |
| 7,457,666 B2 | 11/2008 | Bohn et al. |
| 7,761,162 B2 | 7/2010 | Dong et al. |
| 7,778,696 B2 | 8/2010 | Sathaye |
| 7,783,355 B2 | 8/2010 | Rueter |
| 7,818,059 B2 | 10/2010 | Rueter et al. |
| 7,831,303 B2 | 11/2010 | Rueter et al. |
| 8,280,509 B2 | 10/2012 | Sathaye |
| 2002/0183798 A1 | 12/2002 | Vonk |
| 2003/0069611 A1 | 4/2003 | Levine |
| 2003/0078627 A1 | 4/2003 | Casavant et al. |
| 2003/0083700 A1 | 5/2003 | Hill |
| 2003/0083712 A1 | 5/2003 | Rueter et al. |
| 2003/0195579 A1 | 10/2003 | Bradley et al. |
| 2003/0204214 A1 | 10/2003 | Ferek-Patric |
| 2004/0030358 A1 * | 2/2004 | Rueter et al. ............ 607/27 |
| 2004/0088019 A1 | 5/2004 | Rueter et al. |
| 2004/0260352 A1 | 12/2004 | Rueter et al. |
| 2005/0021095 A1 | 1/2005 | Rueter et al. |
| 2005/0159785 A1 | 7/2005 | Rueter |
| 2005/0222630 A1 | 10/2005 | Schermeier et al. |
| 2006/0155338 A1 | 7/2006 | Mongeon et al. |
| 2006/0241710 A1 | 10/2006 | Rueter |
| 2006/0247705 A1 | 11/2006 | Rueter et al. |
| 2012/0109259 A1 | 5/2012 | Bond et al. |
| 2013/0090702 A1 | 4/2013 | Mongeon et al. |

OTHER PUBLICATIONS (PCT/US2015/027055) PCT Notification of Transmittal of the International Search Report and the Written Opinion of the International Searching Authority, Mailed Sep. 30, 2015, 9 pages.

Demmer, et al., "Method and Apparatus for Detecting Loss of Capture", U.S. Appl. No. 14/261,776, filed Apr. 25, 2014, 44 pages.

* cited by examiner

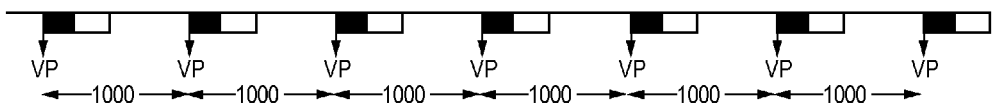
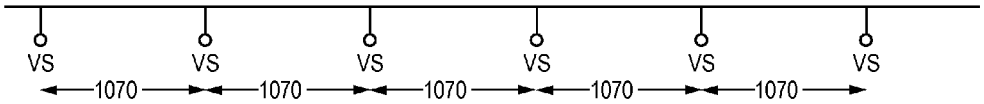
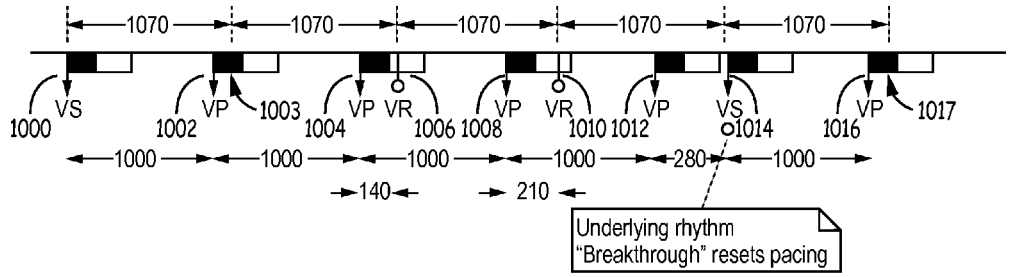

After the first VS in this example, the underlying rate falls into blanking, then generates VRs at constant intervals until the underlying rate marches its way out of the refractory period and generates a VS. Since the interval from the first VS to the first VR is 2X the interval between the subsequent VRs and between the final VR and final VS, and since 1X that interval from the first VS would land in blanking, the algorithm would conclude that capture has possibly been lost.

FIG. 8

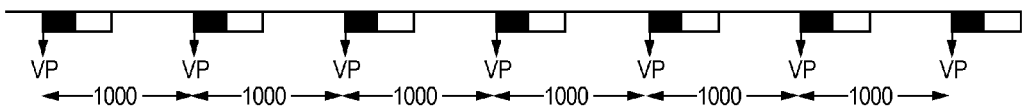
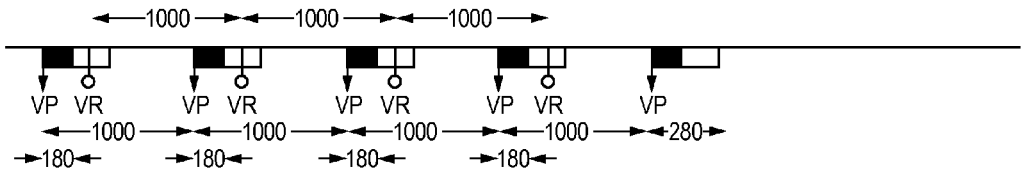
FIG. 10

METHOD AND APPARATUS FOR DETECTING LOSS OF CAPTURE

CROSS-REFERENCE TO RELATED APPLICATIONS

This application claims the benefit of U.S. Provisional Application No. 61/912,189, filed on Feb. 24, 2014. The disclosure of the above application is incorporated herein by reference in its entirety.

TECHNICAL FIELD

This disclosure relates to implantable medical devices and, more particularly, to implantable medical devices.

BACKGROUND

A variety of medical devices for delivering a therapy and/or monitoring a physiological condition have been used clinically or proposed for clinical use in patients. Examples include medical devices that deliver therapy to and/or monitor conditions associated with the heart, muscle, nerve, brain, stomach or other organs or tissue. Some therapies include the delivery of electrical signals, e.g., stimulation, to such organs or tissues. Some medical devices may employ one or more elongated electrical leads carrying electrodes for the delivery of therapeutic electrical signals to such organs or tissues, electrodes for sensing intrinsic electrical signals within the patient, which may be generated by such organs or tissue, and/or other sensors for sensing physiological parameters of a patient. Some medical devices may be "leadless" and include one or more electrodes on an outer housing of the medical device to deliver therapeutic electrical signals to organs or tissues and/or sense intrinsic electrical signals or physiological parameters of a patient.

Medical leads may be configured to allow electrodes or other sensors to be positioned at desired locations for delivery of therapeutic electrical signals or sensing. For example, electrodes or sensors may be carried at a distal portion of a lead. A proximal portion of the lead may be coupled to a medical device housing, which may contain circuitry such as signal generation and/or sensing circuitry. In some cases, the medical leads and the medical device housing are implantable within the patient, while in other cases percutaneous leads may be implanted and connected to a medical device housing outside of the patient. Medical devices with a housing configured for implantation within the patient may be referred to as implantable medical devices. Leadless medical devices are typically implantable medical devices positioned within or adjacent to organs or tissues within a patient for delivery of therapeutic electrical signals or sensing. In some example, leadless implantable medical devices may be anchored to a wall of an organ or to tissue via a fixation mechanism.

Implantable cardiac pacemakers or cardioverter-defibrillators, for example, provide therapeutic electrical signals to the heart, e.g., via electrodes carried by one or more medical leads or via electrodes on an outer housing of a leadless implantable medical device. The therapeutic electrical signals may include pulses for pacing, or shocks for cardioversion or defibrillation. In some cases, a medical device may sense intrinsic depolarizations of the heart, and control delivery of therapeutic signals to the heart based on the sensed depolarizations. Upon detection of an abnormal rhythm, such as bradycardia, tachycardia or fibrillation, an appropriate therapeutic electrical signal or signals may be delivered to restore or maintain a more normal rhythm. For example, in some cases, an implantable medical device may deliver pacing stimulation to the heart of the patient upon detecting tachycardia or bradycardia, and deliver cardioversion or defibrillation shocks to the heart upon detecting fibrillation.

In general, implantable medical devices require a small housing form factor to enable an unobtrusive implantation within a patient. In the case of leadless implantable medical devices, the housing form factor must be extremely small to enable implantation within or adjacent to organs or tissue. For example, a leadless pacemaker may be implanted directly into a ventricle of the heart. Battery usage is always a concern when designing implantable medical devices, but this concern is increased for small form factor devices that can only accommodate a small battery canister.

Currently, many implantable devices attempt to minimize battery drain by means of capture management testing, as described in U.S. Pat. Nos. 5,601,615, 5,766,230, 6,553,259, 7,280,868, 7,457,666, and 761,162, incorporated herein by reference in their entireties. Such tests determine the pacing pulse threshold parameters (typically voltage and pulse width) necessary to capture the chamber of the heart being paced. These tests are also referred to as threshold tests.

The devices typically thereafter set the actual parameters to a higher energy level than the determined threshold parameters, typically to a higher voltage. By this mechanism, the devices provide a safety margin which decreases the likelihood that changes in the underlying condition of the patient's heart will result in a loss of capture. Such capture management tests may be performed according to defined pre-programmed schedules or in response to events indicating that capture is no longer reliably occurring Correspondingly, many devices include the associated capability to detect loss of capture. Such devices are disclosed in the patents cited above. Actual loss of capture may be detected on a beat to beat basis or by changes in detected cardiac rhythm. Detected loss of capture may trigger the performance of a threshold test, as discussed in the above-cited patents. The result will typically be a resetting of pacing parameters to parameters that provide the defined safety margin or by resetting to the maximum energy level deliverable by the device, whichever is less.

SUMMARY

The details of one or more aspects of the disclosure are set forth in the accompanying drawings and the description below. Other features, objects, and advantages of the disclosure will be apparent from the description and drawings, and from the claims.

In order to develop further miniaturized pacing devices such as leadless pacemakers, methods of further reducing unneeded current drain are highly desirable. In many contemporary devices, a substantial amount of battery capacity is spent by pacing at large voltage margin (safety margin) over the pacing threshold. However, reducing the safety margin correspondingly brings an increased risk of loss of capture.

A leadless pacemaker system that may particularly benefit from inclusion of the present invention may be, for example, a single chamber pacemaker that is entirely contained in a single small (e.g. <1 cc) capsule. Due to its small size, a small battery is required and excess power consumption is correspondingly a large concern. To reduce excess power consumption, a device incorporating the present invention preferably employs capture management testing to adjust the pacing output to the lowest reasonably safe voltage (i.e. the smallest reasonable safety margin over the detected threshold). By providing a mechanism for identifying potential loss of capture, the present invention further assists in increasing safety even at very low margins.

A preferred embodiment of the present invention is intended to allow reduction of the safety margin while adding security that loss of capture will be promptly detected and rectified. The intended result is an increase in battery life and the corresponding capability of further miniaturization.

A preferred embodiment of the present invention monitors for evidence that the patient's underlying rhythm is occurring despite the presence of pacing. Because this situation is indicative of a loss of pacing capture, it can be used to identify potential loss of capture and start a new capture management test. This mechanism is substantially less complicated than detection of loss of capture on a beat by beat basis as discussed in the above cited patents, and this brings with it an additional opportunity for energy savings.

Many current devices employ capture management tests that rely on the presence of stable cardiac rhythms as a prerequisite to testing. Because emergence of the patient's underlying rhythm may appear to be an unstable rhythm to the device, such a situation may in some cases cause capture management threshold tests to abort.

One preferred mechanism for identifying loss of capture according to the present invention is by employing a stability check. The stability check may look for an asynchronous underlying rhythm between sensed events (i.e. sensed depolarizations of the relevant heart chamber) by "ignoring" the timing of paced events (i.e. delivered pacing pulses), identifying refractory sensed events occurring at regular intervals with respect to non-refractory sensed events and accounting for intrinsic events that would have occurred in blanking. In response to detection of an asynchronous underlying rhythm, the stability check mechanism may be used as a trigger to indicate when a capture management threshold test should be run. It may also be used to indicate that the support cycles of a capture management threshold test should use a higher pacing amplitude than the current amplitude setting. It may also be used to indicate that a higher pacing voltage should be used while searching for a stable rhythm prior to a capture management threshold test.

The present invention may be employed as part of or in conjunction with any of the various known capture management threshold tests as discussed in the patents cited above. It may also be used in conjunction with alternative loss of capture mechanisms as described in the patents cited above. The invention is believed beneficial in the context of any pacing device that adjust pacing pulse energy to maintain capture.

For patients with a reasonably stable intrinsic rhythm where the intrinsic rhythm is not an exact multiple of the pacing rate, the stability check mechanism is intended to detect complete loss of capture or intermittent loss of capture where a majority of paces in a given period do not capture.

Because T-wave over-sensing may result in a series of consistently timed refractory sensed ventricular events, the invention preferably provides a mechanism of distinguishing this situation from loss of capture. One mechanism of accomplishing this is to eliminate the situation in which ventricular sensed events occur at the same rate as delivered ventricular pacing pulses and/or in which refractory ventricular sensed events occur at consistent intervals following delivered pacing pulses.

BRIEF DESCRIPTION OF DRAWINGS

FIG. 8 is a timing diagram illustrating operation of a preferred embodiment of the invention in response to complete loss of capture.

FIG. 10 is a timing diagram illustrating operation of a preferred embodiment of the invention in response to T-wave over-sensing.

DETAILED DESCRIPTION

Figure 1:
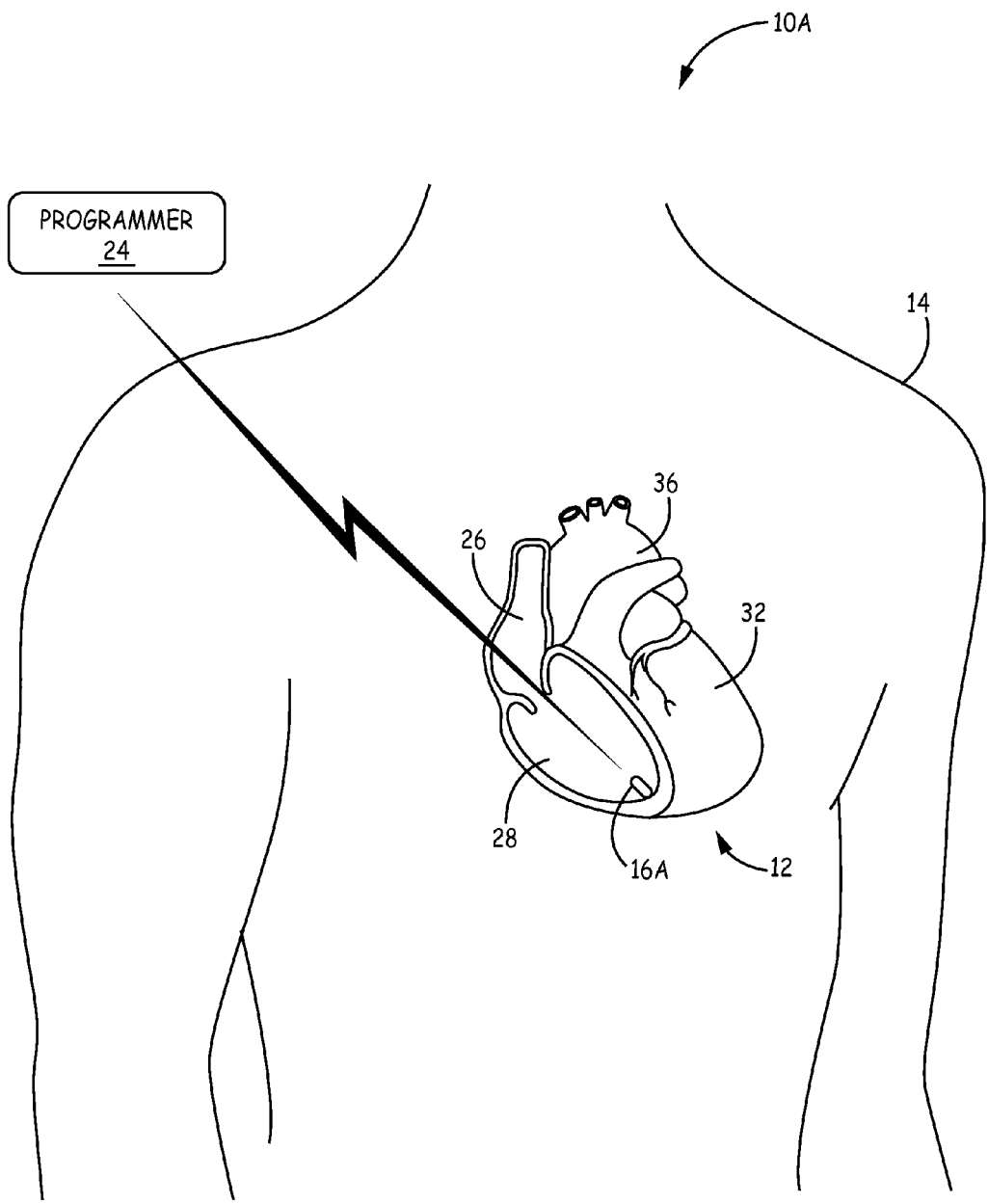
FIG. 1 is a diagram illustrating an example therapy system comprising a leadless implantable medical device (IMD) that may be used to monitor one or more physiological parameters of a patient and/or provide therapy to the heart of a patient.

FIG. 1 is a diagram illustrating an exemplary therapy system 10A that may be used to monitor one or more physiological parameters of patient 14 and/or to provide therapy to heart 12 of patient 14. Therapy system 10A includes an implantable medical device (IMD) 16A, which is coupled to programmer 24. IMD 16A may be an implantable leadless pacemaker that provides electrical signals to heart 12 via one or more electrodes (not shown in FIG. 1) on its outer housing. Additionally or alternatively, IMD 16A may sense electrical signals attendant to the depolarization and repolarization of heart 12 via electrodes on its outer housing. In some examples, IMD 16A provides pacing pulses to heart 12 based on the electrical signals sensed within heart 12. Patient 14 is ordinarily, but not necessarily, a human patient.

In the example of FIG. 1, IMD 16A is positioned wholly within heart 12 with one end proximate to the apex of right ventricle 28 to provide right ventricular (RV) pacing. Although IMD 16A is shown within heart 12 and proximate to the apex of right ventricle 28 in the example of FIG. 1, IMD 16A may be positioned at any other location outside or within heart 12. For example, IMD 16A may be positioned outside or within right atrium 26, left atrium 36, and/or left ventricle 32, e.g., to provide right atrial, left atrial, and left ventricular pacing, respectively. Depending in the location of implant, IMD 16A may include other stimulation functionalities. For example, IMD 16A may provide atrioventricular nodal stimulation, fat pad stimulation, vagal stimulation, or other types of neurostimulation. In other examples, IMD 16A may be a monitor that senses one or more parameters of heart 12 and may not provide any stimulation functionality. In some examples, system 10A may include a plurality of leadless IMDs 16A, e.g., to provide stimulation and/or sensing at a variety of locations.

FIG. 1 further depicts programmer 24 in communication with IMD 16A. In some examples, programmer 24 comprises a handheld computing device, computer workstation, or networked computing device. Programmer 24 includes a user interface that presents information to and receives input from a user. It should be noted that the user may also interact with programmer 24 remotely via a networked computing device.

A user, such as a physician, technician, surgeon, electrophysiologist, other clinician, or patient, interacts with programmer 24 to communicate with IMD 16A. For example, the user may interact with programmer 24 to retrieve physiological or diagnostic information from IMD 16A. A user may also interact with programmer 24 to program IMD 16A, e.g., select values for operational parameters of the IMD 16A. For example, the user may use programmer 24 to retrieve information from IMD 16A regarding the rhythm of heart 12, trends therein over time, or arrhythmic episodes.

As another example, the user may use programmer 24 to retrieve information from IMD 16A regarding other sensed physiological parameters of patient 14 or information derived from sensed physiological parameters, such intracardiac or intravascular pressure, activity, posture, respiration, tissue perfusion, heart sounds, cardiac electrogram (EGM), intracardiac impedance, or thoracic impedance. In some examples, the user may use programmer 24 to retrieve information from IMD 16A regarding the performance or integrity of IMD 16A or other components of system 10A, or a power source of IMD 16A. As another example, the user may interact with programmer 24 to program, e.g., select parameters for, therapies provided by IMD 16A, such as pacing and, optionally, neurostimulation.

IMD 16A and programmer 24 may communicate via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 16A implant site in order to improve the quality or security of communication between IMD 16A and programmer 24.

Figure 2:
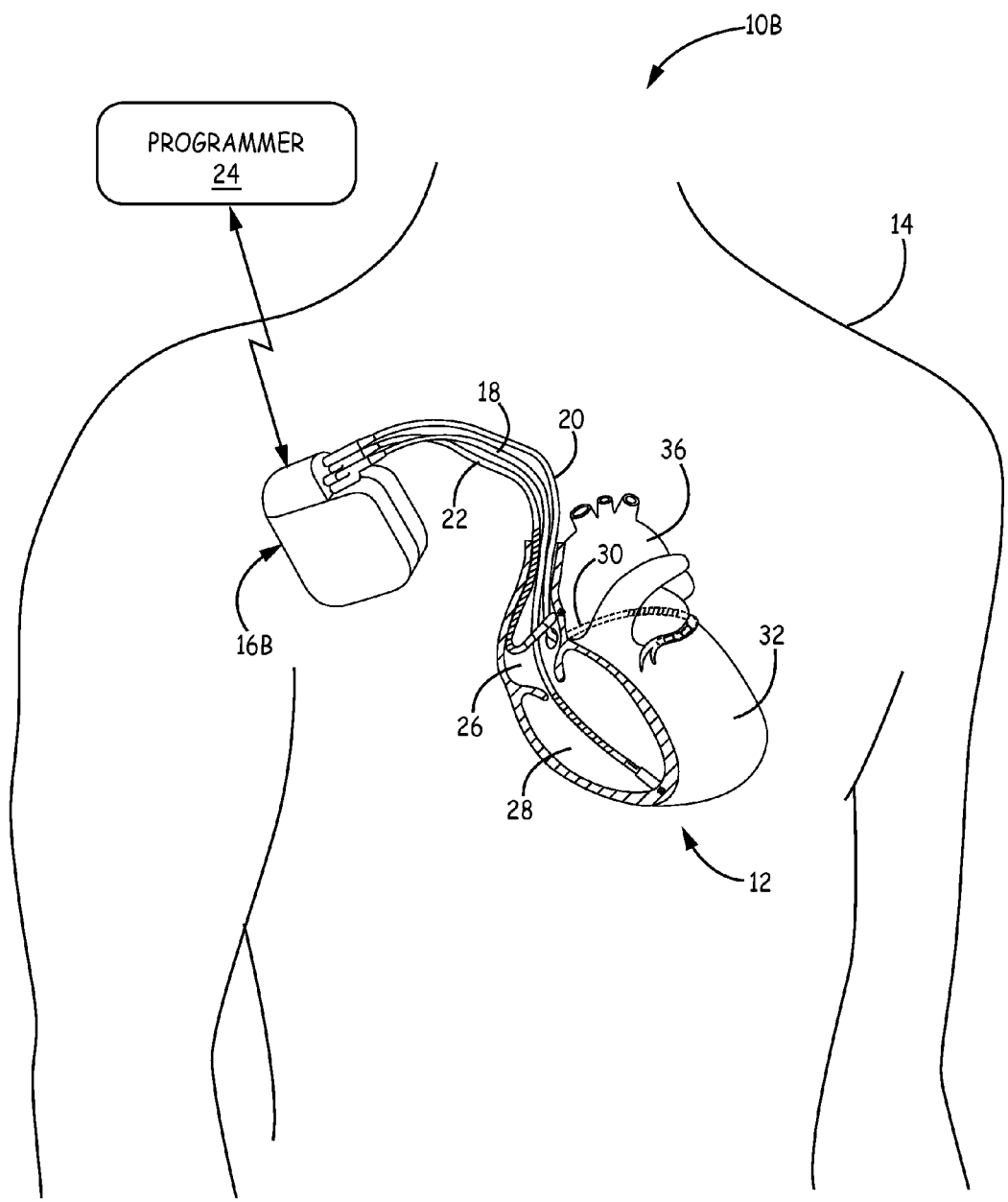
FIG. 2 is a diagram illustrating another example therapy system comprising an IMD coupled to a plurality of leads that may be used to monitor one or more physiological parameters of a patient and/or provide therapy to the heart of a patient.

FIG. 2 is a diagram illustrating another exemplary therapy system 10B that may be used to monitor one or more physiological parameters of patient 14 and/or to provide therapy to heart 12 of patient 14. Therapy system 10B includes IMD 16B, which is coupled to leads 18, 20, and 22, and programmer 24. In one example, IMD 16B may be an implantable pacemaker that provides electrical signals to heart 12 via electrodes coupled to one or more of leads 18, 20, and 22. In addition to pacing therapy, IMD 16B may deliver neurostimulation signals. In some examples, IMD 16B may also include cardioversion and/or defibrillation functionalities. In other examples, IMD 16B may not provide any stimulation functionalities and, instead, may be a dedicated monitoring device. Patient 14 is ordinarily, but not necessarily, a human patient.

Leads 18, 20, 22 extend into the heart 12 of patient 14 to sense electrical activity of heart 12 and/or deliver electrical stimulation to heart 12. In the example shown in FIG. 2, right ventricular (RV) lead 18 extends through one or more veins (not shown), the superior vena cava (not shown), right atrium 26, and into right ventricle 28. RV lead 18 may be used to deliver RV pacing to heart 12. Left ventricular (LV) lead 20 extends through one or more veins, the vena cava, right atrium 26, and into the coronary sinus 30 to a region adjacent to the free wall of left ventricle 32 of heart 12. LV lead 20 may be used to deliver LV pacing to heart 12. Right atrial (RA) lead 22 extends through one or more veins and the vena cava, and into the right atrium 26 of heart 12. RA lead 22 may be used to deliver RA pacing to heart 12.

In some examples, system 10B may additionally or alternatively include one or more leads or lead segments (not shown in FIG. 2) that deploy one or more electrodes within the vena cava or other vein, or within or near the aorta. Furthermore, in another example, system 10B may additionally or alternatively include one or more additional intravenous or extravascular leads or lead segments that deploy one or more electrodes epicardially, e.g., near an epicardial fat pad, or proximate to the vagus nerve. In other examples, system 10B need not include one of ventricular leads 18 and 20.

IMD 16B may sense electrical signals attendant to the depolarization and repolarization of heart 12 via electrodes (described in further detail with respect to FIG. 4) coupled to at least one of the leads 18, 20, 22. In some examples, IMD 16B provides pacing pulses to heart 12 based on the electrical signals sensed within heart 12. The configurations of electrodes used by IMD 16B for sensing and pacing may be unipolar or bipolar.

IMD 16B may also provide neurostimulation therapy, defibrillation therapy and/or cardioversion therapy via electrodes located on at least one of the leads 18, 20, 22. For example, IMD 16B may deliver defibrillation therapy to heart 12 in the form of electrical pulses upon detecting ventricular fibrillation of ventricles 28 and 32. In some examples, IMD 16B may be programmed to deliver a progression of therapies, e.g., pulses with increasing energy levels, until a fibrillation of heart 12 is stopped. As another example, IMD 16B may deliver cardioversion or ATP in response to detecting ventricular tachycardia, such as tachycardia of ventricles 28 and 32.

As described above with respect to IMD 16A of FIG. 1, programmer 24 may also be used to communicate with IMD 16B. In addition to the functions described with respect to IMD 16A of FIG. 1, a user may use programmer 24 to retrieve information from IMD 16B regarding the performance or integrity of leads 18, 20 and 22 and may interact with programmer 24 to program, e.g., select parameters for, any additional therapies provided by IMD 16B, such as cardioversion and/or defibrillation.

In addition to the functions described with respect to IMD 16A of FIG. 1, a user may use programmer 24 to retrieve information from IMD 16B regarding the performance or integrity of leads 18, 20 and 22 and may interact with programmer 24 to program, e.g., select parameters for, any additional therapies provided by IMD 16B, such as cardioversion and/or defibrillation.

Figure 3:
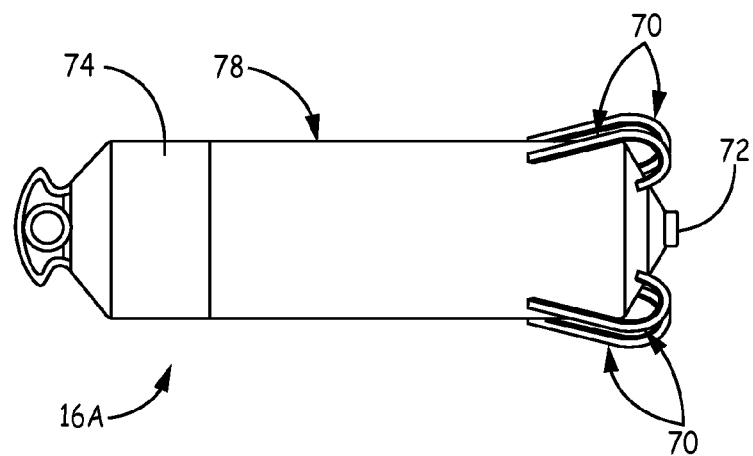
FIG. 3 illustrates the IMD of FIG. 1 in more detail

FIG. 3 is a diagram illustrating leadless IMD 16 of FIG. 1 in further detail. In the example of FIG. 3, leadless IMD 16A includes fixation mechanism 70. Fixation mechanism 70 may anchor leadless IMD 16A to a wall of heart 12. For example, fixation mechanism 70 may take the form of multiple tines that may be inserted into a wall of heart 12 to fix leadless IMD 16A at the apex of right ventricle 28. Alternatively, other structures of fixation mechanism 70, e.g., adhesive, sutures, or screws may be utilized. In some examples, fixation mechanism is conductive and may be used as an electrode, e.g., to deliver therapeutic electrical signals to heart 12 and/or sense intrinsic depolarizations of heart 12.

Leadless IMD 16A may also include electrodes 72 and 74 at a tip of outer housing 78. Electrodes 72 and 74 may be used to deliver therapeutic electrical signals to heart 12 and/or sense intrinsic depolarizations of heart 12. Electrodes 72 and 74 may be formed integrally with an outer surface of hermetically-sealed housing 78 of IMD 16A or otherwise coupled to housing 78. In this manner, electrodes 72 and 74 may be referred to as housing electrodes. In some examples, housing electrodes 72 and 74 are defined by uninsulated portions of an outward facing portion of housing 78 of IMD 16A. Other division between insulated and uninsulated portions of housing 78 may be employed to define a different number or configuration of housing electrodes. For example, in an alternative configuration, IMD 16A may include a single housing electrode that comprises substantially all of housing 78, and may be used in combination with an electrode formed by fixation mechanism 70 for sensing and/or delivery of therapy.

Figure 4:
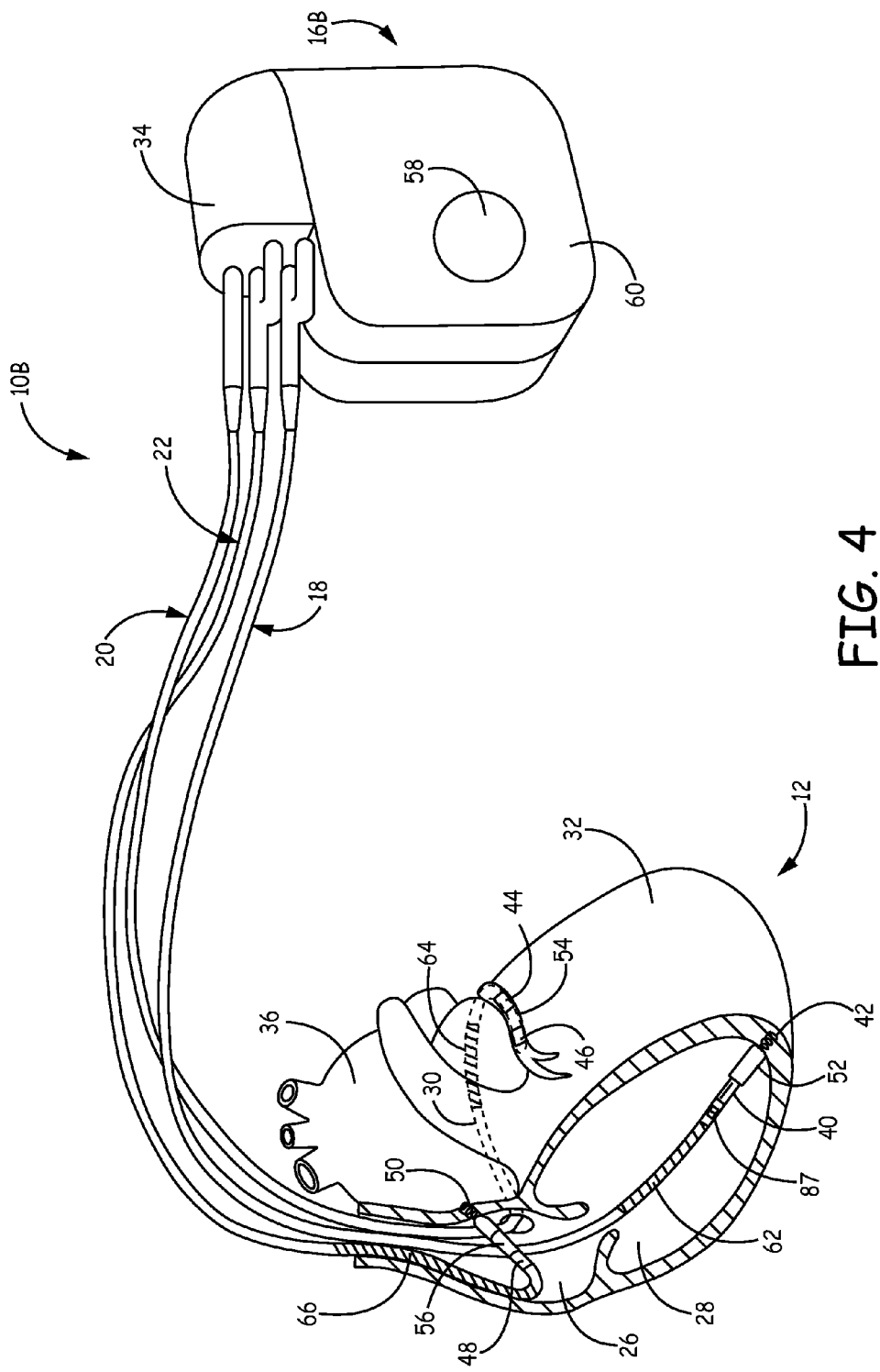
FIG. 4 illustrates the IMD of FIG. 2 in more detail

FIG. 4 is a diagram illustrating IMD 16B and leads 18, 20, 22 of therapy system 10B of FIG. 2 in greater detail. Leads 18, 20, 22 may be electrically coupled to a signal generator and a sensing module of IMD 16B via connector block 34. In some examples, proximal ends of leads 18, 20, 22 may include electrical contacts that electrically couple to respective electrical contacts within connector block 34 of IMD 16B. In some examples, a single connector, e.g., an IS-4 or DF-4 connector, may connect multiple electrical contacts to connector block 34. In addition, in some examples, leads 18, 20, 22 may be mechanically coupled to connector block 34 with the aid of set screws, connection pins, snap connectors, or another suitable mechanical coupling mechanism.

Each of the leads 18, 20, 22 includes an elongated insulative lead body, which may carry a number of concentric coiled conductors separated from one another by tubular insulative sheaths. Bipolar electrodes 40 and 42 are located adjacent to a distal end of lead 18 in right ventricle 28. In addition, bipolar electrodes 44 and 46 are located adjacent to a distal end of lead 20 in left ventricle 32 and bipolar electrodes 48 and 50 are located adjacent to a distal end of lead 22 in right atrium 26. In the illustrated example, there are no electrodes located in left atrium 36. However, other examples may include electrodes in left atrium 36.

Electrodes 40, 44, and 48 may take the form of ring electrodes, and electrodes 42, 46, and 50 may take the form of extendable helix tip electrodes mounted retractably within insulative electrode heads 52, 54, and 56, respectively. In some examples, one or more of electrodes 42, 46, and 50 may take the form of pre-exposed helix tip electrodes. In other examples, one or more of electrodes 42, 46, and 50 may take the form of small circular electrodes at the tip of a tined lead or other fixation element. Leads 18, 20, 22 also include elongated electrodes 62, 64, 66, respectively, which may take the form of a coil. Each of the electrodes 40, 42, 44, 46, 48, 50, 62, 64, and 66 may be electrically coupled to a respective one of the coiled conductors within the lead body of its associated lead 18, 20, 22, and thereby coupled to respective ones of the electrical contacts on the proximal end of leads 18, 20, 22.

In some examples, as illustrated in FIG. 4, IMD 16B includes one or more housing electrodes, such as housing electrode 58, which may be formed integrally with an outer surface of hermetically-sealed housing 60 of IMD 16B or otherwise coupled to housing 60. In some examples, housing electrode 58 is defined by an uninsulated portion of an outward facing portion of housing 60 of IMD 16B. Other division between insulated and uninsulated portions of housing 60 may be employed to define two or more housing electrodes. In some examples, housing electrode 58 comprises substantially all of housing 60.

IMD 16B may sense electrical signals attendant to the depolarization and repolarization of heart 12 via electrodes 40, 42, 44, 46, 48, 50, 58, 62, 64, and 66. The electrical signals are conducted to IMD 16B from the electrodes via conductors within the respective leads 18, 20, 22 or, in the case of housing electrode 58, a conductor coupled to housing electrode 58. IMD 16B may sense such electrical signals via any bipolar combination of electrodes 40, 42, 44, 46, 48, 50, 58, 62, 64, and 66. Furthermore, any of the electrodes 40, 42, 44, 46, 48, 50, 58, 62, 64, and 66 may be used for unipolar sensing in combination with housing electrode 58.

In some examples, IMD 16B delivers pacing pulses via bipolar combinations of electrodes 40, 42, 44, 46, 48 and 50 to produce depolarization of cardiac tissue of heart 12. In some examples, IMD 16B delivers pacing pulses via any of electrodes 40, 42, 44, 46, 48 and 50 in combination with housing electrode 58 in a unipolar configuration.

Furthermore, IMD 16B may deliver defibrillation pulses to heart 12 via any combination of elongated electrodes 62, 64, 66, and housing electrode 58. Electrodes 58, 62, 64, 66 may also be used to deliver cardioversion pulses to heart 12. Electrodes 62, 64, 66 may be fabricated from any suitable electrically conductive material, such as, but not limited to, platinum, platinum alloy or other materials known to be usable in implantable defibrillation electrodes.

The configuration of the systems illustrated in FIGS. 1-4 are merely exemplary. In other examples, a system may include percutaneous leads, epicardial leads and/or patch electrodes instead of or in addition to the transvenous leads 18 and 22 illustrated in FIG. 2. Further, the IMD need not be implanted within patient 14. In examples in which the IMD is not implanted in a patient, the IMD may deliver defibrillation pulses and other therapies to heart 12 via percutaneous leads that extend through the skin of patient 14 to a variety of positions within or outside of heart 12.

In addition, in other examples, a system may include any suitable number of leads coupled to IMD 16B, and each of the leads may extend to any location within or proximate to heart 12. For example, other examples of systems may include three transvenous leads located as illustrated in FIGS. 2 and 4, and an additional lead located within or proximate to left atrium 36. Other examples of systems may include a single lead that extends from IMD 16B into right atrium 26 or right ventricle 28, or two leads that extend into a respective one of the right ventricle 26 and right atrium 26. Any electrodes located on these additional leads may be used in sensing and/or stimulation configurations.

Figure 5:
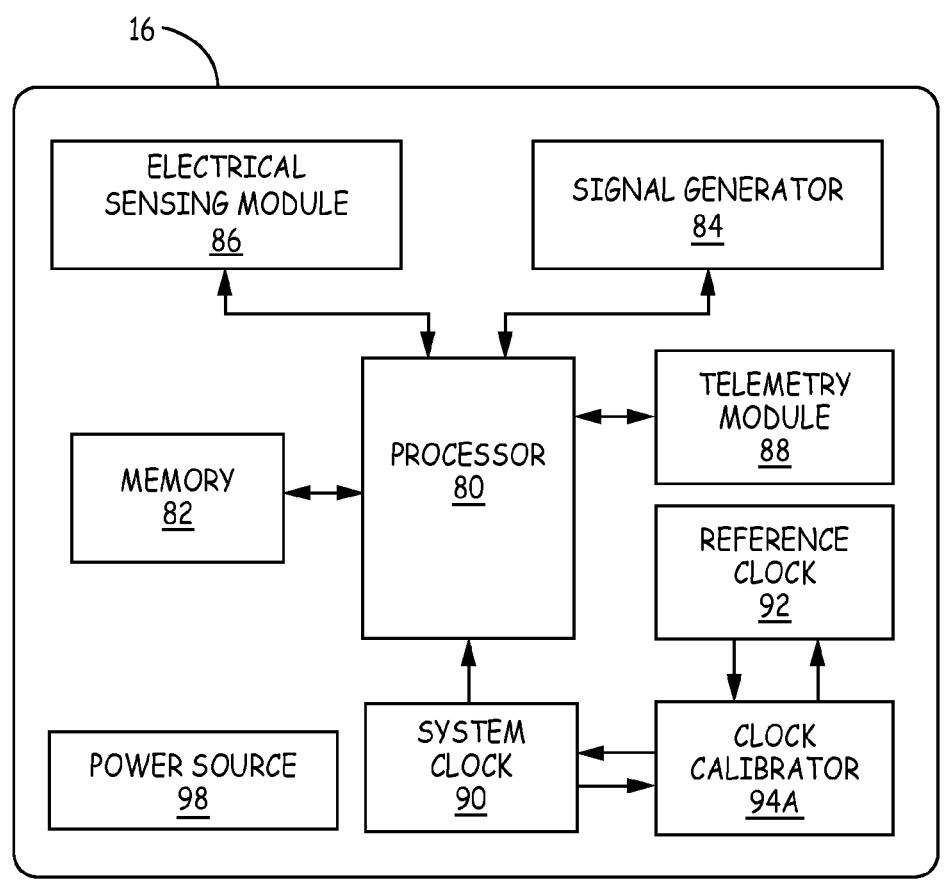
FIG. 5 is a functional block diagram illustrating an example configuration of an IMD.

FIG. 5 is a functional block diagram illustrating an example configuration of IMD 16, which may be IMD 16A of FIGS. 1 and 3 or IMD 16B of FIGS. 2 and 4. In the example illustrated by FIG. 4, IMD 16 includes a processor 80, memory 82, signal generator 84, electrical sensing module 86, telemetry module 88, system clock 90, reference clock 92, clock calibrator 94A, and power source 98. Memory 82 may include computer-readable instructions that, when executed by processor 80, cause IMD 16 and processor 80 to perform various functions attributed to IMD 16 and processor 80 herein. Memory 82 may comprise a computer-readable storage medium, including any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog storage media.

Figure 6:
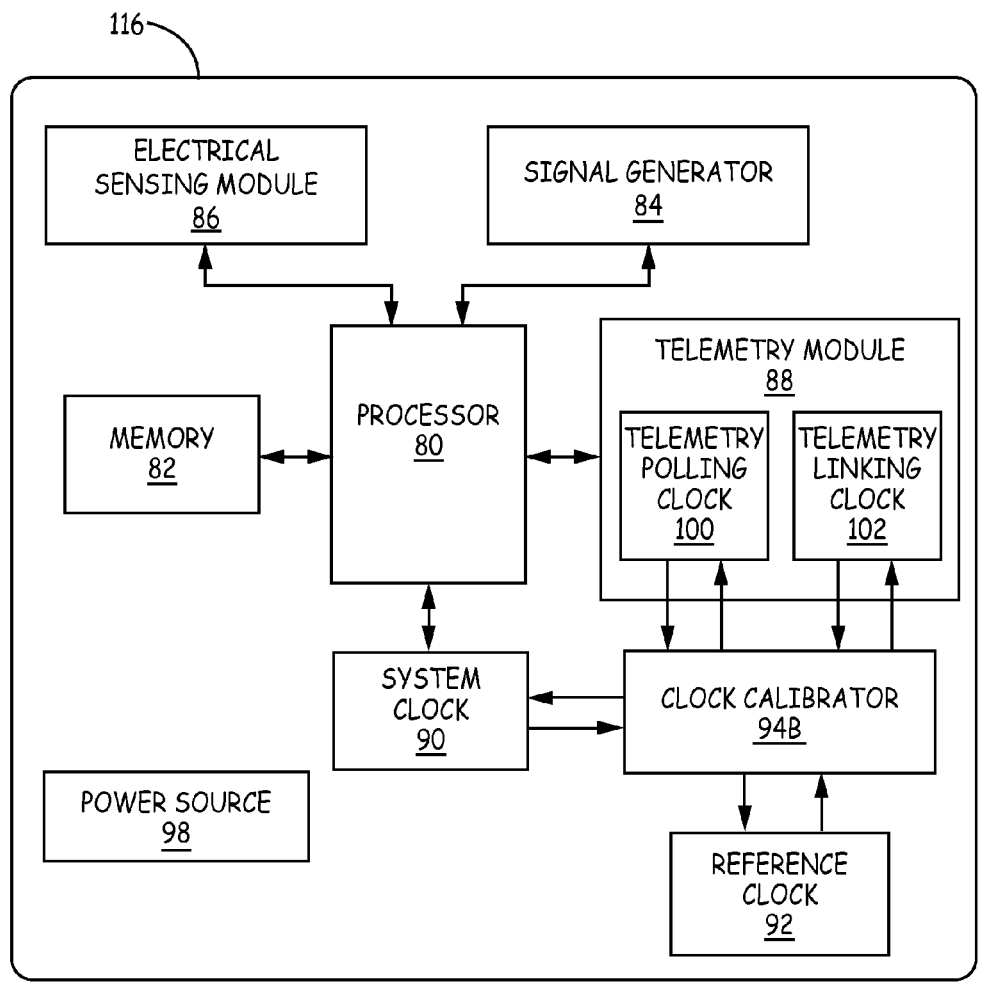
FIG. 6 is a block diagram of an example external programmer that facilitates user communication with an IMD.

Processor 80 may include any one or more of a microprocessor, a controller, a digital signal processor (DSP), an application specific integrated circuit (ASIC), a field-programmable gate array (FPGA), or equivalent discrete or integrated logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 in this disclosure may be embodied as software, firmware, hardware or any combination thereof. IMD 16 also includes a sensing integrity module 90, as illustrated in FIG. 6, which may be implemented by processor 80, e.g., as a hardware component of processor 80, or a software component executed by processor 80.

Processor 80 controls signal generator 84 to deliver stimulation therapy to heart 12 according to operational parameters or programs, which may be stored in memory 82. For example, processor 80 may control signal generator 84 to deliver electrical pulses with the amplitudes, pulse widths, frequency, or electrode polarities specified by the selected one or more therapy programs.

In the particular case of cardiac pacing, intervals controlled by the processor 80 would typically include the pacing rate (escape interval duration), refractory periods during which sensed depolarization events do not reset timing of the escape interval, blanking periods during which depolarization events are not sensed.

Signal generator 84, as well as electrical sensing module 86, is electrically coupled to electrodes of IMD 16 and/or leads coupled to IMD 16. In the example of leadless IMD 16A of FIG. 3, signal generator 84 and electrical sensing module 86 are coupled to electrodes 72 and 74, e.g., via conductors disposed within housing 78 of leadless IMD 16A. In examples in which fixation mechanism 70 functions as an electrode, signal generator 84 and electrical sensing module 86 may also be coupled to fixation mechanism 70, e.g., via a conductor disposed within housing 78 of leadless IMD 16A. In the example of IMD 16B of FIG. 2, signal generator 84 and electrical sensing module 86 are coupled to electrodes 40, 42, 48, 50, 56 and 62 via conductors of the respective lead 18 or 22, or, in the case of housing electrode 58, via an electrical conductor disposed within housing 60 of IMD 16B.

In the example illustrated in FIG. 4, signal generator 84 is configured to generate and deliver electrical stimulation therapy to heart 12. For example, signal generator 84 may deliver pacing, cardioversion, defibrillation, and/or neurostimulation therapy via at least a subset of the available electrodes. In some examples, signal generator 84 delivers one or more of these types of stimulation in the form of electrical pulses. In other examples, signal generator 84 may deliver one or more of these types of stimulation in the form of other signals, such as sine waves, square waves, or other substantially continuous time signals.

Signal generator 84 may include a switch module and processor 80 may use the switch module to select, e.g., via a data/address bus, which of the available electrodes are used to deliver stimulation signals, e.g., pacing, cardioversion, defibrillation, and/or neurostimulation signals. The switch module may include a switch array, switch matrix, multiplexer, or any other type of switching device suitable to selectively couple a signal to selected electrodes.

Electrical sensing module 86 monitors signals from at least a subset of the available electrodes in order to monitor electrical activity of heart 12. Electrical sensing module 86 may also include a switch module to select which of the available electrodes are used to sense the heart activity. In some examples, processor 80 may select the electrodes that function as sense electrodes, i.e., select the sensing configuration, via the switch module within electrical sensing module 86, e.g., by providing signals via a data/address bus.

In some examples, electrical sensing module 86 includes multiple detection channels, each of which may comprise an amplifier. Each sensing channel may detect electrical activity in respective chambers of heart 12, and may be configured to detect either R-waves or P-waves. In some examples, electrical sensing module 86 or processor 80 may include an analog-to-digital converter for digitizing the signal received from a sensing channel for electrogram (EGM) signal processing by processor 80. In response to the signals from processor 80, the switch module within electrical sensing module 86 may couple the outputs from the selected electrodes to one of the detection channels or the analog-to-digital converter.

During pacing, escape interval counters maintained by processor 80 may be reset upon sensing of R-waves and P-waves with respective detection channels of electrical sensing module 86. Signal generator 84 may include pacer output circuits that are coupled, e.g., selectively by a switching module, to any combination of the available electrodes appropriate for delivery of a bipolar or unipolar pacing pulse to one or more of the chambers of heart 12. Processor 80 may control signal generator 84 to deliver a pacing pulse to a chamber upon expiration of an escape interval. Processor 80 may reset the escape interval counters upon the generation of pacing pulses by signal generator 84, or detection of an intrinsic depolarization in a chamber, and thereby control the basic timing of cardiac pacing functions. The escape interval counters may include P-P, V-V, RV-LV, A-V, A-RV, or A-LV interval counters, as examples. The value of the count present in the escape interval counters when reset by sensed R-waves and P-waves may be used by processor 80 to measure the durations of R-R intervals, P-P intervals, P-R intervals and R-P intervals. Processor 80 may use the count in the interval counters to detect heart rate, such as an atrial rate or ventricular rate.

In the particular context of the present invention, the processor also determines intervals between successive sensed and paced events in a given chamber, including events sensed during refractory periods. For example, in the case in which the invention is embodied in a ventricular pacemaker, the processor would calculate V-pace to v-pace intervals, V-sense to V-sense intervals, V-pace to V-sense intervals and V-sense to V-pace intervals. In such cases, the V-sense events would include ventricular evens sensed both in and out of the ventricular refractory period. The processor 80 stores these intervals in memory 82 for analysis according to the present invention.

Operation of the present invention to detect loss of capture will typically be controlled and defined by software instructions stored in memory 82 and implemented by processor 80. Such instructions would correspond to the functional flowcharts of FIG. 11-14, discussed below.

Telemetry module 88 includes any suitable hardware, firmware, software or any combination thereof for communicating with another device, such as programmer 24 (FIGS. 1 and 2). Under the control of processor 80, telemetry module 88 may receive downlink telemetry from and send uplink telemetry to programmer 24 with the aid of an antenna, which may be internal and/or external. Processor 80 may provide the data to be uplinked to programmer 24 and receive downlinked data from programmer 24 via an address/data bus. In some examples, telemetry module 88 may provide received data to processor 80 via a multiplexer.

The clocking system of IMD 16 includes system clock 90, reference clock 92, and clock calibrator 94A. Each of the clocks described herein comprise oscillators that may operate at different frequencies with different accuracies and different power requirements. IMD 16 may require an extremely small housing form factor, especially in the case of leadless IMD 16A of FIGS. 1 and 3. For example, leadless IMD 16 may have a form factor of less than 1 cubic centimeter. Due to the small form factor requirements, IMD 16 may only be able to accommodate a small battery canister such that current drain within IMD 16 must by extremely low. One aspect of reducing power in IMD 16 is to minimize current drain by the clocking system.

Figure 12:
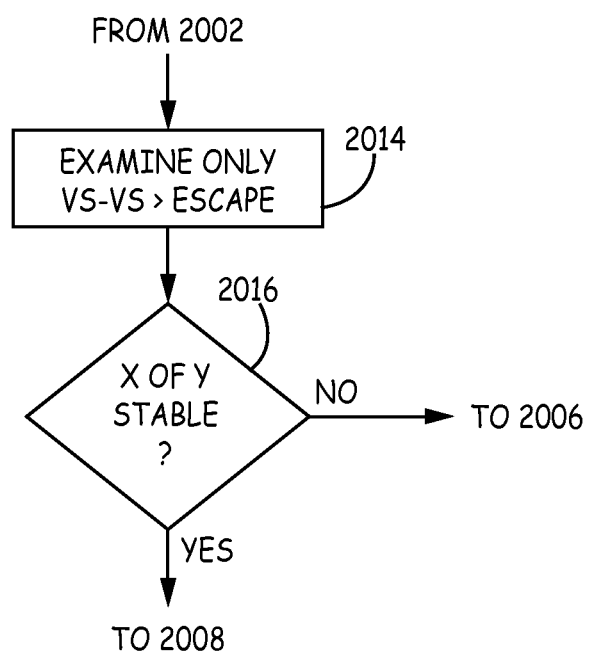
FIG. 12 is a functional flow chart illustrating operation of a stability test according to a first preferred embodiment of the invention.

A detailed description of the use of the clocking system to reduce power consumption is set forth in US Patent Publication No. US 20120109259 A1, incorporated herein by reference in its entirety FIG. 6 is a functional block diagram of an example configuration of programmer 24. As shown in FIG. 12, programmer 24 includes processor 140, memory 142, user interface 144, telemetry module 146, and power source 148. Programmer 24 may be a dedicated hardware device with dedicated software for programming of IMD 16. Alternatively, programmer 24 may be an off-the-shelf computing device running an application that enables programmer 24 to program IMD 16. In other examples, programmer 24 may be used to program IMD 16 of FIG. 7 in a substantially similar manner as IMD 16 of FIG. 6.

A user may use programmer 24 to select therapy programs (e.g., sets of stimulation parameters), generate new therapy programs, or modify therapy programs for IMD 16. The clinician may interact with programmer 24 via user interface 144, which may include a display to present a graphical user interface to a user, and a keypad or another mechanism for receiving input from a user.

Processor 140 can take the form one or more microprocessors, DSPs, ASICs, FPGAs, programmable logic circuitry, or the like, and the functions attributed to processor 140 in this disclosure may be embodied as hardware, firmware, software or any combination thereof. Memory 142 may store instructions and information that cause processor 140 to provide the functionality ascribed to programmer 24 in this disclosure. Memory 142 may include any fixed or removable magnetic, optical, or electrical media, such as RAM, ROM, CD-ROM, hard or floppy magnetic disks, EEPROM, or the like. Memory 142 may also include a removable memory portion that may be used to provide memory updates or increases in memory capacities. A removable memory may also allow patient data to be easily transferred to another computing device, or to be removed before programmer 24 is used to program therapy for another patient. Memory 142 may also store information that controls therapy delivery by IMD 16, such as stimulation parameter values.

Programmer 24 may communicate wirelessly with IMD 16, such as using RF communication or proximal inductive interaction. This wireless communication is possible through the use of telemetry module 146, which may be coupled to an internal antenna or an external antenna. An external antenna that is coupled to programmer 24 may correspond to the programming head that may be placed over heart 12, as described above with reference to FIG. 1. Telemetry module 146 may be similar to telemetry module 88 of IMD 16 (FIG. 6).

Telemetry module 146 may also be configured to communicate with another computing device via wireless communication techniques, or direct communication through a wired connection. Examples of local wireless communication techniques that may be employed to facilitate communication between programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 24 without needing to establish a secure wireless connection. An additional computing device in communication with programmer 24 may be a networked device such as a server capable of processing information retrieved from IMD 16.

Figure 7:
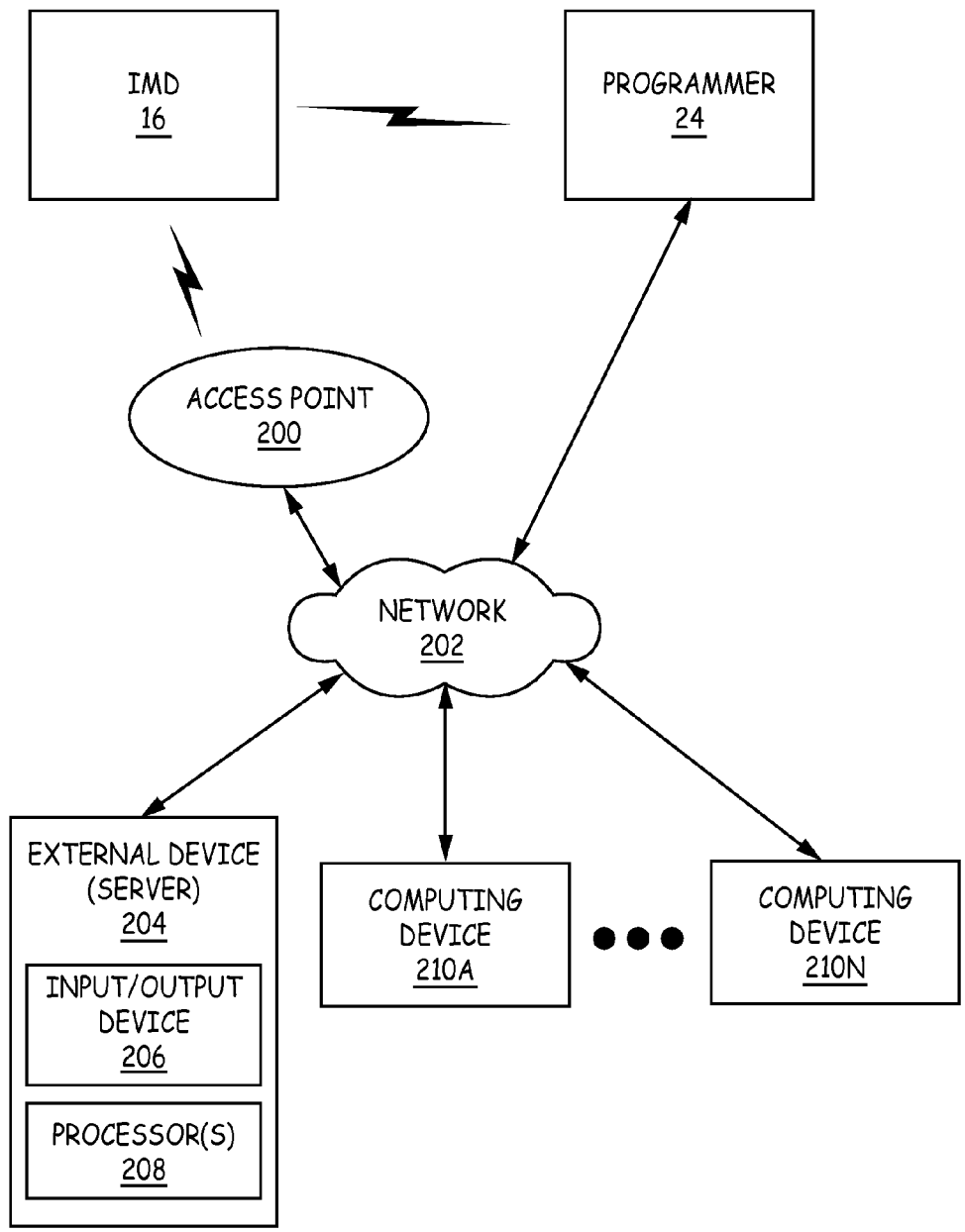
FIG. 7 is a block diagram illustrating an example system that includes an external device, such as a server, and one or more computing devices that are coupled to an IMD and programmer via a network.

FIG. 7 is a block diagram illustrating an example system that includes an external device, such as a server 204, and one or more computing devices 210A-210N, that are coupled to the IMD 16 and programmer 24 (shown in FIGS. 1 and 2) via a network 202. In other examples, the system of FIG. 13 may include IMD 116 of FIG. 7 in a substantially similar manner as IMD 16 of FIG. 6.

Figure 13:
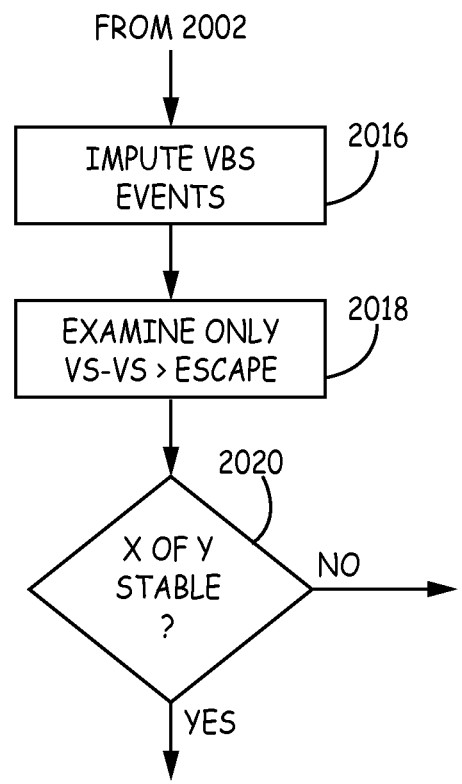
FIG. 13 is a functional flow chart illustrating operation of a stability test according to a second preferred embodiment of the invention.

In this example, IMD 16 may use its telemetry module 88 to communicate with programmer 24 via a first wireless connection, and to communication with an access point 200 via a second wireless connection. In the example of FIG. 13, access point 200, programmer 24, server 204, and computing devices 210A-210N are interconnected, and able to communicate with each other, through network 202. In some cases, one or more of access point 200, programmer 24, server 204, and computing devices 210A-210N may be coupled to network 202 through one or more wireless connections. IMD 16, programmer 24, server 204, and computing devices 210A-210N may each comprise one or more processors, such as one or more microprocessors, DSPs, ASICs, FPGAs, programmable logic circuitry, or the like, that may perform various functions and operations, such as those described herein.

Access point 200 may comprise a device that connects to network 202 via any of a variety of connections, such as telephone dial-up, digital subscriber line (DSL), or cable modem connections. In other examples, access point 200 may be coupled to network 202 through different forms of connections, including wired or wireless connections. In some examples, access point 200 may be co-located with patient 14 and may comprise one or more programming units and/or computing devices (e.g., one or more monitoring units) that may perform various functions and operations described herein. For example, access point 200 may include a home-monitoring unit that is co-located with patient 14 and that may monitor the activity of IMD 16. In some examples, server 204 or computing devices 210 may control or perform any of the various functions or operations described herein.

In some cases, server 204 may be configured to provide a secure storage site for data that has been collected from IMD 16 and/or programmer 24. Network 202 may comprise a local area network, wide area network, or global network, such as the Internet. In some cases, programmer 24 or server 206 may assemble data in web pages or other documents for viewing by trained professionals, such as clinicians, via viewing terminals associated with computing devices 210A-210N. The illustrated system of FIG. 13 may be implemented, in some aspects, with general network technology and functionality similar to that provided by the Medtronic CareLink® Network developed by Medtronic, Inc., of Minneapolis, Minn.

In one or more examples, the functions described above may be implemented in hardware, software, firmware, or any combination thereof. If implemented in software, the functions may be stored on or transmitted over as one or more instructions or code on a computer-readable medium. Computer-readable media may include computer data storage media or communication media including any medium that facilitates transfer of a computer program from one place to another. Data storage media may be any available media that can be accessed by one or more computers or one or more processors to retrieve instructions, code and/or data structures for implementation of the techniques described in this disclosure. By way of example, and not limitation, such computer-readable media can comprise RAM, ROM, EEPROM, CD-ROM or other optical disk storage, magnetic disk storage, or other magnetic storage devices, flash memory, or any other medium that can be used to carry or store desired program code in the form of instructions or data structures and that can be accessed by a computer. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

The code may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. In addition, in some aspects, the functionality described herein may be provided within dedicated hardware and/or software modules. Also, the techniques could be fully implemented in one or more circuits or logic elements.

Operation of preferred embodiments of the present invention to detect loss of capture is described below in conjunction with FIGS. 8-14. The specific embodiments described are directed to loss of capture detection in a ventricular pacemaker, but the same mechanism may be employed to detect loss of capture in atrial pacemakers as well. The embodiments of FIGS. 8-14 should be considered exemplary rather than limiting with regard to the invention as claimed.

FIG. 8 shows a timing diagram illustrating operation of a preferred embodiment of the invention in response to complete loss of capture. The upper strip illustrates the basic time intervals defined by the processor 80 in conjunction with simple VVI pacing, including the escape interval between delivered pacing pulses (VP) of 1000 ms (60 bpm pacing rate). The blanking periods following each delivered ventricular pacing pulses (VP) are illustrated by black boxes. The refractory periods correspond to the gray shaded boxes following the black boxes. Ventricular depolarizations (VS) cannot be sensed by the device during the blanking periods. Ventricular depolarizations (VS) can be sensed during the refractory periods but do not re-start the escape interval.

The middle strip illustrates the timing of intrinsic ventricular depolarizations (VS) at a rate less than the pacing rate, e.g. at intervals of 1070 ms.

The lower strip illustrates the inter-action of a pacemaker operating according to the upper strip in the presence of an intrinsic rhythm as illustrated in the middle strip, in the situation in which none of the delivered pacing pulses (VP) are effective to capture the heart. Starting with the initial VS 1000, the pacemaker times an escape interval of 1000 ms. which expires with delivery of the first VP 1002. Because the next intrinsic depolarization 1003 at 1070 ms. falls within the blanking period, it is not detected by the device. The next VP is correspondingly delivered at 1004, with the next sensed ventricular depolarization (VR) 1006 falling within the refractory period. Such events are also referred to a refractory sensed events. This event is sensed but does not affect timing of the next pacing pulse 1008, which is correspondingly followed by another refractory sensed event VR 1010. Following VP1012, the next sensed ventricular event VS 1014 falls outside the refractory period and thus resets timing of the escape interval, resulting in delivery of a ventricular pacing pulse at 1016, followed by an un-sensed intrinsic depolarization at 1017, during the blanking period.

The result of non-capture as illustrated is the occurrence of multiple sensed ventricular events separated by relatively consistent intervals longer than the escape interval of the pacemaker. Preferred embodiments of the invention as discussed below are directed to identifying this pattern of events as indicative of loss of capture.

This pattern of events would be clearer if the intrinsic ventricular events at 1-03 and 1017 could have been sensed. Therefore, in a preferred embodiment of the invention, the occurrence of sensed events during blanking periods is imputed responsive to the detected rhythm suggesting the likely occurrence of such events. In this embodiment, as discussed in more detail below in conjunction with FIGS. 13 and 14, the imputed sensed events (ventricular blanking sensed events or VBS events) are considered along with the refractory sensed events (VR) and the non-refractory sensed events (VS) in analyzing the pattern.

Because capture loss may be incomplete, in some cases the intervals between sensed events, even when including the imputed VBS events, may not all be consistent in duration. As such, the present invention preferably applies an X of Y criterion, finding loss of capture (total or partial) when x of y previous intervals between sensed events are relatively consistent in duration. In some preferred embodiments, the intervals considered for analysis may be limited to intervals longer than the escape interval, in order to avoid detecting T-wave over-sensing as loss of capture. In other embodiments, consistent VP to VR intervals may be disqualified as possible indications of loss of capture.

Figure 9:
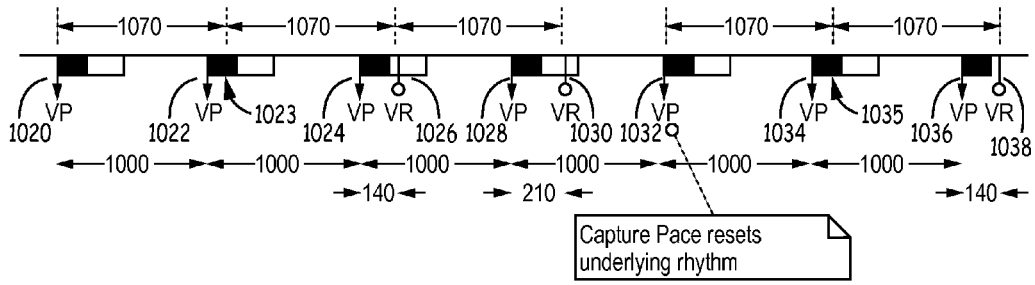
FIG. 9 is a timing diagram illustrating operation of a preferred embodiment of the invention in response to partial loss of capture.

FIG. 9 shows a timing diagram illustrating operation of a preferred embodiment of the invention in response to partial loss of capture. The upper and middle strips correspond to those of FIG. 8.

The lower strip illustrates the inter-action of a pacemaker operating according to the upper strip in the presence of an intrinsic rhythm as illustrated in the middle strip, in the situation in which some but not all of the delivered pacing pulses (VP) are effective to capture the heart. Starting with the initial VP 1020 which does capture the heart, resetting the intrinsic timing of the ventricle, the pacemaker times an escape interval of 1000 ms. which expires with delivery of VP 1022, which does not capture the heart. Because the next intrinsic depolarization 1023 at 1070 ms. falls within the blanking period, it is not detected by the device. The next VP is correspondingly delivered at 1024, with the next sensed ventricular depolarization (VR) 1026 falling within the refractory period. This event is sensed but does not affect timing of the next pacing pulse 1028, which is correspondingly followed by another refractory sensed event VR 1030. The following VP1032 captures the heart, resetting the intrinsic timing of the ventricle. Because the next intrinsic depolarization 1035 at 1070 ms. falls within the blanking period following VP 1034, it is not detected by the device. The next VP is correspondingly delivered at 101036, with the next sensed ventricular depolarization (VR) 1038 falling within the refractory period.

Again, the pattern of V-sense to V-sense intervals which are consistent and longer than the pacemakers escape interval appears. As discussed above in conjunction with FIG. 8, the ability to impute the occurrence of VBS events makes the pattern clearer. The X of Y criterion discussed in conjunction with FIG. 8 will still apply in this situation, allowing the detection of non-capture.

FIG. 10 is a timing diagram illustrating the effect of T-wave over-sensing. The top strip corresponds to the top strips of FIGS. 8 and 9. The lower strip illustrates the situation in which T-wave over-sensing results in sensed ventricular events (VR) following all or most ventricular pacing pulses VP. In this event, there will be a substantial number of VS-sense to V-sense events separated by consistent intervals. In preferred embodiments of the invention, this rhythm is rejected as indicative of capture because the V-sense to V-sense intervals are not asynchronous to the pacing pulse. As discussed below, such rhythms may be rejected because the VP to VR interval is consistent or because the VR to VR interval is consistent with the pacemaker's escape interval. Again, an X of Y criterion may be applied, so that the rhythm is rejected as indicative of non-capture if X of Y previous VP to VR intervals are consistent or if X of Y VR-VR intervals are consistent with the escape interval. Application of the X of Y criterion in these cases also allows for the fact the T-wave over-sensing may not occur following each delivered pacing pulse.

Figure 11:
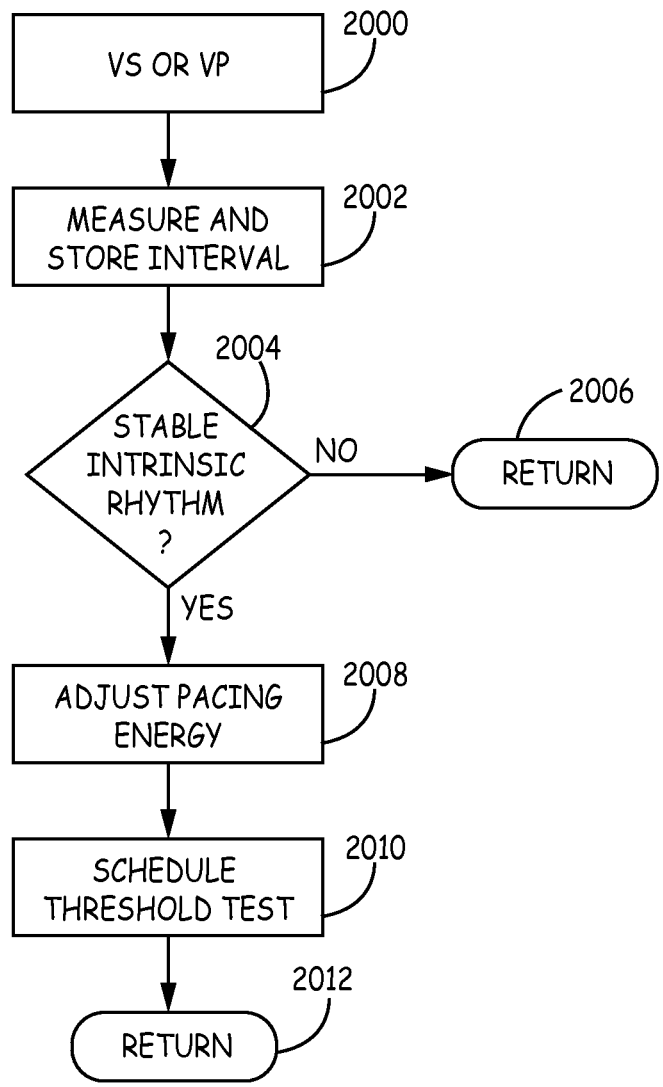
FIG. 11 is a functional flow chart illustrating over-all operation of a preferred embodiment of the invention.

FIG. 11 is a functional flow chart illustrating over-all operation of a preferred embodiment of the invention. FIG. 11 illustrates the general mechanism of a preferred embodiment of the invention. In one sense, it may be understood as illustrating a sub-routine stored in memory 82 and executed by processor 80 in response to occurrence of a sensed or paced event at 2000. In alternative embodiments, however, equivalent functions could be performed by dedicated digital circuitry. The specific implementation is not believed critical to the invention as a whole.

At 2002, responsive to the sensed ventricular event (refractory or non-refractory) or the paced event, the interval separating the event from the previous event is measured and stored in memory 82. At 2004, the preceding series of stored intervals between events is analyzed to determine whether X of Y of them are consistent in timing. This aspect of the invention is referred to above as the "stability test". For purposes of this analysis, a group of intervals with stable or consistent timing may be determined by determining that the intervals are less than a defined time interval difference from one another or that they are less than a defined percentage difference from one another. These requirements may optionally be set by the physician following an analysis of the regularity of the patient's intrinsic rate or may be pre-set.

As discussed below, the analysis at 2004 may include operations which impute the occurrences of sensed events during blanking periods (VBS), which are considered along with the other sensed events for purposes of the analysis. As also discussed below, this analysis may include operations which reject occurrences of T-wave over-sensing as indicative of loss of capture.

If the stability test at 2004 does not indicate emergence of an underlying rhythm indicative of non-capture, the operation of the device returns to the next scheduled operation at 2006. If the stability test at 2004 does indicate emergence of an underlying rhythm indicative of non-capture, the operation of the device is modified at 2008 and/or 2010 by one or both the increasing the pacing pulse energy pending the next scheduled threshold test, by increasing the pulse energy employed during the next scheduled threshold test and/o by rescheduling the next threshold test to an earlier time. The device then returns to the next scheduled operation at 2012.

FIG. 12 is a functional flow chart illustrating operation of a stability test according to a first preferred embodiment of the invention. In response to measurement of an interval at 2002, only intervals exceeding the escape interval are considered at 2014. This step is optional and may be deleted. At 2016, the device checks to see if X of Y of the preceding V-sense to V-sense intervals considered are consistent in timing as discussed above FIG. 13 is a functional flow chart illustrating operation of a stability test according to a second preferred embodiment of the invention. In this embodiment, in response to measurement of an interval at 2002, depolarizations during the blanking period are imputed at 2014 if appropriate. A mechanism for accomplishing this is discussed in conjunction with FIG. 14. Intervals between the imputed sensed events and previous and subsequent sensed events are calculated and stored for use in performing the stability test. At 2014, only intervals exceeding the escape interval are identified for consideration in performing the stability test. This step is optional and may be deleted. At 2016, the device checks to see if X of Y of the preceding V-sense to V-sense intervals considered are consistent in timing as discussed above.

Figure 14:
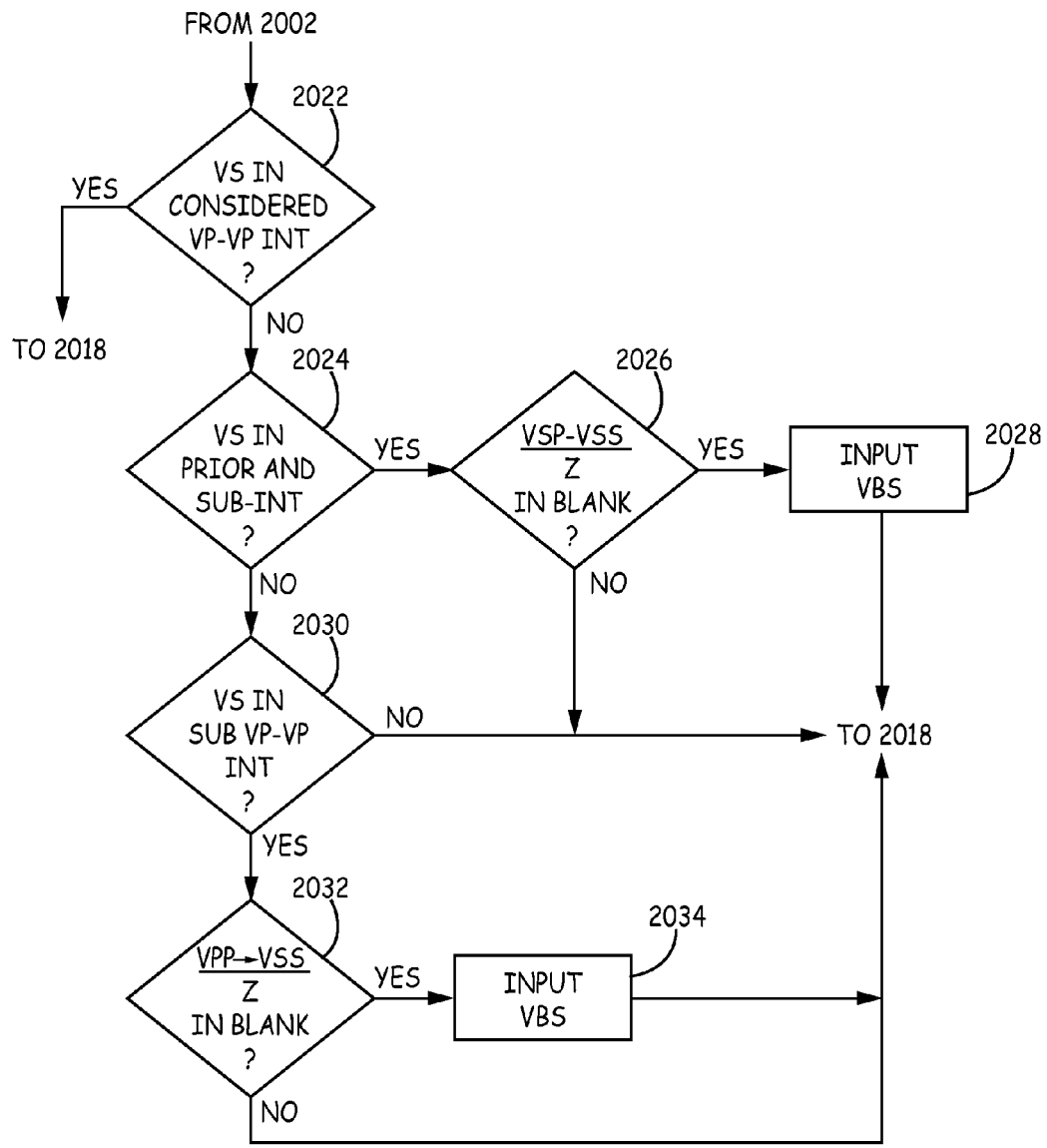
FIG. 14 is a functional flow chart illustrating operation of imputation of ventricular blanking period sensing according to the embodiment of FIG. 13.

FIG. 14 is a functional flow chart illustrating operation of imputation of ventricular blanking period sensing according to the embodiment of FIG. 13. In this embodiment, in response to measurement of an interval at 2002, the device at considers the VP-VP interval prior to the interval ending in the detected paced or sensed event. If a V-sense event occurred during this interval, the device simply returns to the next scheduled operation at 2018. If there was no V-sense event, the device considers the stored interval preceding the considered VP-VP interval, (the prior interval) and the interval ending in the most recent event (the subsequent interval. If a V-sense event occurs in both the prior and subsequent intervals as determined at 2024, the device determines whether a time halfway between the V-sense event in the prior interval (VSP) and the V-sense event in the subsequent interval (VSS) would fall within the blanking period of the VP-VP interval being considered at 2026. If so, a ventricular sense during the blanking period is imputed at the halfway point (VBS) and intervals between the VBS and prior and subsequent V-senses are calculated and stored at 2028 for use in the stability test. the device then returns to the next scheduled operation at 2018.

If a V-sense event occurs only in the subsequent interval as determined at 2030, the device determines whether a time halfway between the V-pace event in the prior interval (VPP) and the V-sense event in the subsequent interval (VSS) would fall within the blanking period of the VP-VP interval being considered at. If so, a ventricular sense during the blanking period is imputed at the halfway point (VBS) and intervals between the VBS and prior and subsequent V-senses are calculated and stored at 2034 for use in the stability test. The device then returns to the next scheduled operation at 2018. Either or both of the mechanisms of 2026 and 2039 for imputing the occurrence of sensed events during the blanking period may be employed.

Figure 15:
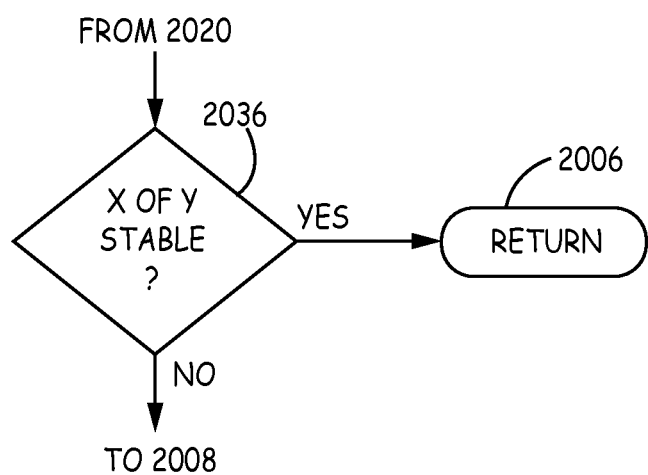
FIG. 15 is a functional flow chart illustrating operation of a mechanism for preventing identification of T-wave oversensing as indicative of loss of capture.

FIG. 15 is a functional flow chart illustrating operation of a mechanism for preventing identification of T-wave oversensing as indicative of loss of capture. This set of operations may be understood in conjunction with any of the stability check tests discussed above, and may be performed before or after the stability tests or as a step of the stability test. For purposes of FIG. 15, it is considered to be performed at 2036 following step 2020 of FIG. 13, responsive to the stability criterion being met. As discussed above such rhythms may be rejected because the VP to VR intervals are consistent or because the VR to VR intervals is consistent with the pacemaker's escape interval. Again, an X of Y criterion may be applied, so that the rhythm is rejected as indicative of non-capture if X of Y previous VP to VR intervals are consistent or if X of Y VR-VR intervals are consistent with the escape interval. Application of the X of Y criterion in these cases also allows for the fact the T-wave over-sensing may not occur following each delivered pacing pulse.

Various examples of the disclosure have been described. These and other examples are within the scope of the following claims.

The invention claimed is:

1. A method for identifying loss of capture in a pacing device, comprising:
   delivering cardiac pacing pulses;
   checking for emergence of a stable asynchronous underlying intrinsic rhythm in the presence of the delivered pacing pulses;
   determining that loss of capture has occurred responsive to emergence of the underlying rhythm; and
   in response to determining that loss of capture has occurred, modifying the pacing provided by device,
   wherein checking for emergence of a stable asynchronous underlying intrinsic rhythm comprises sensing occurrences of cardiac events and measuring only intervals between the sensed cardiac events,
   wherein the cardiac pacing pulses are delivered separated by escape intervals, and
   wherein measuring intervals between the sensed cardiac events comprises measuring only the intervals which exceed the escape intervals.

2. A method according to claim 1 wherein modifying the pacing provided by device comprises performing a pacing threshold check and adjusting energy levels of the delivered pacing pulses in response thereto.

3. A method for identifying loss of capture in a pacing device, comprising:
   delivering cardiac pacing pulses;
   checking for emergence of a stable asynchronous underlying intrinsic rhythm in the presence of the delivered pacing pulses;
   determining that loss of capture has occurred responsive to emergence of the underlying rhythm;
   in response to determining that loss of capture has occurred, modifying the pacing provided by device; and
   further comprising imputing occurrences cardiac of events during periods during which sensing is not possible,
   wherein checking for emergence of a stable asynchronous underlying intrinsic rhythm comprises sensing occurrences of cardiac events measuring intervals between the sensed cardiac events and between the sensed and imputed cardiac events.

4. A method according to claim 3 wherein the cardiac pacing pulses are delivered separated by escape intervals and wherein measuring intervals between the sensed cardiac events comprises measuring only the intervals which exceed the escape intervals.

5. A method according to claim 3 wherein occurrences of cardiac events are imputed based upon timing of sensed cardiac events occurring before and after intervals between delivered pacing pulses in which no cardiac events are sensed.

6. An apparatus for identifying loss of capture in a pacing device, comprising:
   means for delivering cardiac pacing pulses;
   means for checking for emergence of a stable asynchronous underlying intrinsic rhythm in the presence of delivered pacing pulses;
   means for determining that loss of capture has occurred responsive to emergence of the underlying rhythm; and
   means responsive determining that loss of capture has occurred for modifying the pacing provided by device,
   wherein checking for emergence of a stable asynchronous underlying intrinsic rhythm comprises sensing occurrences of cardiac events and measuring only intervals between the sensed cardiac events,
   wherein the cardiac pacing pulses are delivered separated by escape intervals, and
   wherein measuring intervals between the sensed cardiac events comprises measuring only the intervals which exceed the escape intervals.

7. An apparatus according to claim 6 wherein modifying the pacing provided by device comprises performing a pacing threshold check and adjusting energy levels of the delivered pacing pulses in response thereto.

8. An apparatus for identifying loss of capture in a pacing device, comprising:
   means for delivering cardiac pacing pulses;
   means for checking for emergence of a stable asynchronous underlying intrinsic rhythm in the presence of delivered pacing pulses;
   means for determining that loss of capture has occurred responsive to emergence of the underlying rhythm;
   means responsive determining that loss of capture has occurred for modifying the pacing provided by device; and
   means for imputing occurrences of cardiac events during periods during which sensing is not possible, wherein checking for emergence of a stable asynchronous underlying intrinsic rhythm comprises sensing occurrences of cardiac events measuring intervals between the sensed cardiac events and between the sensed and imputed cardiac events.

9. An apparatus according to claim 8 wherein the cardiac pacing pulses are delivered separated by escape intervals and wherein measuring intervals between the sensed cardiac events comprises measuring only the intervals which exceed the escape intervals.

10. An apparatus according to claim 8 wherein occurrences of cardiac events are imputed based upon timing of sensed cardiac events occurring before and after intervals between delivered pacing pulses in which no cardiac events are sensed.

11. A non-transitory program medium comprising instructions for identifying loss of capture in a pacing device, comprising:
   instructions for checking for emergence of a stable asynchronous underlying intrinsic rhythm in the presence of delivered pacing pulses;
   instructions for determining that loss of capture has occurred responsive to emergence of the underlying rhythm; and
   instructions executed responsive determining that loss of capture has occurred for modifying the pacing provided by device,
   wherein checking for emergence of a stable asynchronous underlying intrinsic rhythm comprises sensing occurrences of cardiac events and measuring only intervals between the sensed cardiac events;

wherein the cardiac pacing pulses are delivered separated by escape intervals, and wherein measuring intervals between the sensed cardiac events comprises measuring only the intervals which exceed the escape intervals.

12. A medium according to claim 11 wherein the instructions for modifying the pacing provided by device comprise instructions to performing a pacing threshold check and instructions for adjusting energy levels of the delivered pacing pulses in response thereto.

13. A method for identifying loss of capture in a pacing device, comprising:

delivering a series of cardiac pacing pulses separated by escape intervals;

checking for emergence of a stable asynchronous underlying intrinsic rhythm in the presence of the series of delivered pacing pulses;

determining that loss of capture has occurred responsive to emergence of the underlying rhythm; and in response to determining that loss of capture has occurred, modifying the pacing provided by device; and wherein checking for emergence of a stable asynchronous underlying intrinsic rhythm comprises sensing occurrences of cardiac events and measuring intervals between the sensed cardiac events; and wherein measuring intervals between the sensed cardiac events comprises measuring intervals which exceed the escape intervals.

14. An apparatus for identifying loss of capture in a pacing device, comprising:

means for delivering a series of cardiac pacing pulses separated by escape intervals;

means for checking for emergence of a stable asynchronous underlying intrinsic rhythm in the presence of the series of delivered pacing pulses;

means for determining that loss of capture has occurred responsive to emergence of the underlying rhythm; and means responsive determining that loss of capture has occurred for modifying the pacing provided by device, wherein checking for emergence of a stable asynchronous underlying intrinsic rhythm comprises sensing occurrences of cardiac events and measuring intervals between the sensed cardiac events, and wherein measuring intervals between the sensed cardiac events comprises measuring intervals which exceed the escape intervals.

* * * * *